United States Patent [19]

Fischer et al.

[11] 3,935,200

[45] Jan. 27, 1976

[54] N,N-DISUBSTITUTED 2,1,3-BENZOTHIADIAZIN-(4)-ONE-2,2-DIOXIDE

[75] Inventors: Adolf Fischer, Mutterstadt; Gerhard Hamprecht, Mannheim; Rolf Huber, Ludwigshafen, all of Germany

[73] Assignee: BASF Aktiengesellschaft, Ludwigshafen, Germany

[22] Filed: Oct. 18, 1974

[21] Appl. No.: 516,072

[30] Foreign Application Priority Data

Nov. 3, 1973  Germany............................ 2355113

[52] U.S. Cl................................. 260/243 R; 71/91
[51] Int. Cl.².......................................... C07D 285/16

[58] Field of Search................................ 260/243 R

[56] References Cited

UNITED STATES PATENTS 3,287,362  11/1966  Hurmen et al...................... 260/243

Primary Examiner—John M. Ford
Attorney, Agent, or Firm—Johnston, Keil, Thompson & Shurtleff

[57] ABSTRACT

New and Valuable substituted 2,1,3-benzothiadiazin-(4)-one-2,2-dioxides having a good herbicidal action and a process for controlling the growth of unwanted plants with these compounds.

9 Claims, No Drawings

N,N-DISUBSTITUTED 2,1,3-BENZOTHIADIAZIN-(4)-ONE-2,2-DIOXIDE

The present invention relates to new and valuable substituted 2,1,3-benzothiadiazin-(4)-one-2,2-dioxides having a herbicidal action, herbicides containing these active ingredients, a process for controlling the growth of unwanted plants with these compounds, and a process for preparing these compounds.

It is known (German No. 1,542,836) to use N-monosubstituted 2,1,3-benzothiadiazin-(4)-one-2,2-dioxides as herbicidal active ingredients. However, their action is not always satisfactory on mono- and dicotyledonous weeds.

We have now found that compounds of the formula

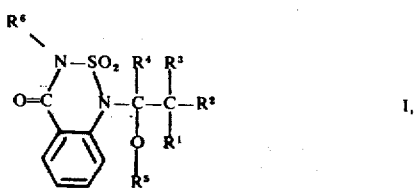

where $R^1$, $R^2$, $R^3$ and $R^4$ are hydrogen or halogen, $R^1$, $R^2$ and $R^4$ may also be a lower unsubstituted or halogen-substituted or halogen-substituted alkyl of 1 to 10 carbon atoms or an aromatic radical, $R^5$ is an unsubstituted or halogen-substituted aliphatic radical of 1 to 20 carbon atoms or an aromatic radical, $R^1$ and $R^5$ may also be portions of an aliphatic ring, and $R^6$ is an unsubstituted or halogen-substituted aliphatic radical of 1 to 10 carbon atoms, have a better herbicidal action than prior art compounds, combined with the same crop plant compatibility.

Compounds of the formula I may be prepared for instance by alkylating substituted 3-alkyl-2,1,3-benzothiadiazin-(4)-one-2,2-dioxides with reactive vinyl ethers. The same compounds are aslo obtained by reacting the alkali metal salts with α-halo ethers.

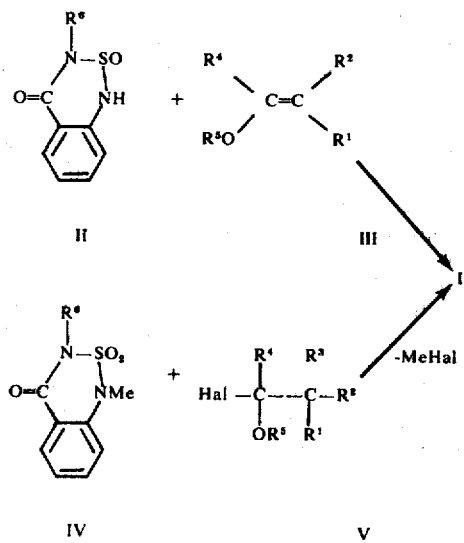

where $R^1$ to $R^6$ have the above meanings, Me is alkali and Hal is halogen.

The 3-alkyl-2,1,3-benzothiadiazin-(4)-one-2,2-dioxides may be prepared by known methods (German No. 1,542,836).

In an embodiment of the invention, a vinyl alkyl or aryl ether of the formula III, where $R^1$ to $R^5$ have the above meanings, if desired diluted with solvent, is poured into a solution of the abovementioned 3-alkyl-2,1,3-benzothiadiazin-(4)-one-2,2-dioxides, and the mixture is stirred for from 30 minutes to 8 hours at 10° to 70°C. If $R^1$ to $R^4$ are hydrogen and $R^5$ is lower alkyl, 30 minutes will be sufficient. If radicals $R^1$ to $R^5$ are larger and sterically bulky, longer heating is necessary. If desired, the reaction may be accelerated by adding acid catalysts and by heating at up to 100°C.

In another, particularly preferred, embodiment, for instance an α-halo ether of the formula V, where $R^1$ to $R^5$ have the above meanings, is poured into a solution of a 1-alkali (or alkaline earth) metal salt of a 3-alkyl-2,1,3-benzothiodiazin-(4)-one-2,2-dioxide of the formula IV, $R^6$ having the above meanings, and the precipitated metal halide is removed. The solution is worked up in conventional manner by concentration to dryness or by suction filtration of the precipitated crystalline end products. To remove impurities it may at times be necessary to wash the solution of the end products in a water-immiscible solvent with dilute alkali and water, followed by drying and concentration. The same end products I are also obtained by reacting α-halo ethers V with starting materials II when an organic tertiary base is used as acid acceptor.

Examples of suitable starting materials of the formula II are:

3-methyl-2,1,3-benzothiadiazin-(4)-one-2,2-dioxide
3-ethyl-2,1,3-benzothiadiazin-(4)-one-2,2-dioxide
3-n-propyl-2,1,3-benzothiadiazin-(4)-one-2,2-dioxide
3-isopropyl-2,1,3-benzothiadiazin-(4)-one-2,2-dioxide
3-n-butyl-2,1,3-benzothiadiazin-(4)-one-2,2-dioxide
3-isobutyl-2,1,3-benzothiadiazin-(4)-one-2,2-dioxide
3-sec-butyl-2,1,3-benzothiadiazin-(4)-one-2,2-dioxide
3-cyclopentyl-2,1,3-benzothiadiazin-(4)-one-2,2-dioxide
3-(3'-pentyl)-2,1,3-benzothiadiazin-(4)-one-2,2-dioxide
3-(2'-methylbutyl-3')-2,1,3-benzothiadiazin-(4)-one-2,2-dioxide
3-(2'-methylbutyl-1')-2,1,3-benzothiadiazin-(4)-one-2,2-dioxide
3-(3'-methylpentyl-2')-2,1,3-benzothiadiazin-(4)-one-2,2-dioxide
3-(2'-methylpentyl-4')-2,1,3-benzothiadiazin-(4)-one-2,2-dioxide
3-(heptyl-3')-2,1,3-benzothiadiazin-(4)-one-2,2-dioxide
3-(3'-methylheptyl-2')-2,1,3-benzothiadiazin-(4)-one-2,2-dioxide
3-(1'-cyclohexylethyl-1')-2,1,3-benzothiadiazin-(4)-one-2,2-dioxide
3-(1'-chloroethyl-2')-2,1,3-benzothiadiazin-(4)-one-2,2-dioxide
3-(2'-chloropropyl-1')-2,1,3-benzothiadiazin-(4)-one-2,2-dioxide
3-(1'-chloropropyl-3')-2,1,3-benzothiadiazin-(4)-one-2,2-dioxide
3-(1'-chloropropyl-2')- and 3-(2'-chloropropyl-1')-2,1,3-benzothiadiazin-(4)-one-2,2-dioxide
3-(1'-chlorobutyl-2')-2,1,3-benzothiadiazin-(4)-one-2,2-dioxide
3-(2'-chloro-2'-methylpropyl-3')-2,1,3-benzothiadiazin-(4)-one-2,2-dioxide
3-(1'-fluoropropyl-2')-2,1,3-benzothiadiazin-(4)-one-2,2-dioxide
3-(2'-fluoropropyl-1')-2,1,3-benzothiadiazin-(4)-one-2,2-dioxide
3-(2'-fluoro-2'-methylpropyl-3')-2,1,3-benzothiadiazin-(4)-one-2,2-dioxide.

As vinyl ethers, the following starting materials of the formula III are preferred:
methyl vinyl ether
ethyl vinyl ether
n-propyl vinyl ether
isopropyl vinyl ether
n-butyl vinyl ether
isobutyl vinyl ether
sec-butyl vinyl ether
tert-butyl vinyl ether
n-amyl vinyl ether
isoamyl vinyl ether
sec-amyl vinyl ether
tert-amyl vinyl ether
neopentyl vinyl ether
hexyl vinyl ether
heptyl vinyl ether
octyl vinyl ether
nonyl vinyl ether
decyl vinyl ether
undecyl vinyl ether
dodecyl vinyl ether
tridecyl vinyl ether
tetradecyl vinyl ether
pentadecyl vinyl ether
hexadecyl vinyl ether
heptadecyl vinyl ether
octadecyl vinyl ether
nonadecyl vinyl ether
n-eicosanyl vinyl ether
3-chloropropyl vinyl ether
1,1-dichloroethyl vinyl ether
phenyl vinyl ether
methyl isopropenyl ether
methyl-(propen-(1)-ether
ethyl-(propen-(1)-yl)-ether
methyl-(buten-(1)-yl)-ether
methyl-(1-methylpropen-(1)-yl)-ether
methyl-(2-methypropen-(1)-yl)-ether
methyl-(1,2-dimethylpropen-(1)-yl)-ether
ethyl-(buten-(1)-yl)-ether
ethyl-(penten-(1)-yl)-ether
ethyl-(hexen-(1)-yl-ether
ethyl-(hepten-(1)-yl)-ether
ethyl-(octen-(1)-yl)-ether
ethyl-(nonen-(1)-ether
ethyl-(decen-(1)-yl)-ether
phenyl-(2-phenylvinyl)-ether
methyl-(buten-(1)-3-onyl)-ether
ethyl-(1-phenyl-2-methylpropen-(1)-yl)-ether
2,3-dihydrofuran
3,4-dihydropyran (2H)
ethyl-(1-phenyl-2-benzoylvinyl)-ether
β-chloro-β-ethoxystyrene
ethyl-(2,2-dichlorovinyl)-ether
propyl-(trifluorovinyl)-ether
pentachloro-1-ethoxybutadiene
ethyl-(1,3,3,3,-tetrafluoro-2-trifluoromethylpropen-(1)-yl)-ether.

Preferred α-halo ethers of the formula V are those obtained by adding hydrogen chloride to the vinyl ethers of the formula III. Also suitable are the following compounds:
1,2-dichloroethylmethyl ether
1,2-dichloroethyl ether
α-chloroisopropylethyl ether
1-chloro-2,2-dimethylpropylmethyl ether
1-chloro-1,2,2-trimethylpropylethyl ether

EXAMPLE 1

23.7 parts (by weight) of vinyl isobutyl ether is introduced at 40°C into a solution of 40 parts of 3-sec-butyl-2,1,3-benzothiadiazin-(4)-one in 200 parts of ethyl acetate. One drop if thionyl chloride is added as catalyst, and the reaction solution is then stirred for 2 hours at 70°C. After having been allowed to cool, the solution is washed twice with 0.5 N caustic solution and twice with water. After drying over magnesium sulfate and concentration in vacuo there is obtained 52 parts (93% of theory) of 1-(α-isobutyloxy)-ethyl-3-sec-butyl-2,1,3-benzothiadiazin-(4)-one-2,2-dioxide as a colorless oil; $n_D^{25}$: 1.5097.

EXAMPLE 2

At 20°C and over a period of 10 minutes, 11 parts of α-chlorodiethyl ether is run into a solution of 24 parts of the 1-sodium salt of 3-isopropyl-2,1,3-benzothiadiazin-(4)-one-2,2-dioxide in 270 prts of acetone. The solution is stirred for 30 minutes at room temperature, the precipitated sodium chloride is filtered off, and the solution is concentrated in vacuo.

The oil which remains is taken up in methylene chloride and washed twice with 0.5 N caustic solution and with water. After drying and concentration in vacuo there is obtained 27.5 parts (96% of theory) of 1-(α-ethoxy)-ethyl-3-isopropyl-2,1,3-benzothiadiazin-(4)-one-2,2-dioxide as a colorless oil; $n_D^{25}$: 1.5235.

EXAMPLE 3

10.9 parts of α-chlrodiethyl ether and 10.9 parts of triethylamine are run, over a period of 10 minutes and through 2 supply lines, into a solution of 24 parts of 3-ispropyl-2,1,3-benzothiadiazin-(4)-one-2,2-dioxide in 300 parts of methylene chloride at 20° to 30°C. The mixture is stirred for 1 hour at room temperature and then extracted first with water, then with 0.3 N caustic solution, and again with water. After drying and concentration the same end product is obtained as in Example 2, in the same yield and with the same purity.

The following compounds corresponding to the formula I may be prepared analogously:

| $R^1$ | $R^2$ | $R^3$ | $R^4$ | $R^5$ | $R^6$ | $n_D^{25}$ |
|---|---|---|---|---|---|---|
| H | H | H | H | $C_2H_5$ | $CH_3$ | 1.5273 |
| H | H | H | H | $C_2H_5$ | $C_2H_5$ | 1.5274 |
| H | H | H | H | $C_2H_5$ | $n-C_3H_7$ | 1.5277 |
| H | H | H | H | $C_2H_5$ | $n-C_4H_9$ | |

1-(2'-methyltetrahydrofuranyl-5')-3-isopropyl-2,1,3-benzothiadiazin-(4)-one-2,2-dioxide, m.p. 116°–118°c 1-(4'-methyltetrahydropyranyl-6')-3-isopropyl-2,1,3-benzothiadiazin-(4)-one-2,2-dioxide, m.p. 108°–114°C 1-(2',2'-dimethyltetrahydrofuranyl-5')-3-isopropyl-2,1,3-benzothiadiazin-(4)-one-2,2-dioxide, m.p. 119°–124°C 1-(α-methoxy-β-chloroethyl)-3-isopropyl-2,1,3-benzothiadiazin-(4)-one-2,2-dioxide, m.p. 109°–111°C.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-oils, etc. and oils of vegetable or animal origin, aliphatic, cyclic and aromatic hydrocarbons such as benzene, toluene, xylene, paraffin, tetrahydronaphthalene, alkylated napthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsions concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

The new compositions have a strong herbicidal action and may therefore be used as weedkillers or for controlling the growth of unwanted plants. Whether the new active ingredients are used as total or selective agents depends in essence of the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
    Cynodon spp.    Dactylis spp.
    Digitaria spp.    Avena spp.
    Echinochloa spp.    Bromus spp.
    Setaria spp.    Uniola spp.
    Panicum spp.    Poa spp.
    Alopecurus spp.    Leptochloa spp.
    Lolium spp.    Brachiaria spp.
    Sorghum spp.    Eleusine spp.
    Agropyron spp.    Cenchrus spp.
    Phalaris spp.    Eragrostis spp.
    Apera spp.    Phragmites communis
    etc.;
Cyperaceae, such as
    Carex spp.    Eleocharis spp.
    Cyperus spp.    Scirpus spp.
    etc.;
dicotyledonous weeds, such as
Malvaceae, e.g.,
    Abutilon theoprasti    Hibiscus spp.
    Sida spp.    Malva spp.
    etc.;
Compositae, such as
    Ambrosia spp.    Centaurea spp.
    Lactuca spp.    Tussilago spp.
    Senecio spp.    Lapsana communis
    Sonchus spp.    Tagetes spp.
    Xanthium spp.    Erigeron spp.
    Iva spp.    Anthemis spp.
    Galinsoga spp.    Matricaria spp.
    Taraxacum spp.    Artemisia spp.
    Chrysanthemum spp.    Bidens spp.
    Cirsium spp.    etc.;
Convolvulaceae, such as
    Convolvulus spp.    Cuscuta spp.
    Ipomoea spp.    Jaquemontia tamnifolia
    etc.;
Cruciferae, such as
    Barbarea vulgaris    Arabidopsis thaliana
    Brassica spp.    Descurainia spp.
    Capsella spp.    Draba spp.
    Sisymbrium spp.    Coronopus didymus
    Thlaspi spp.    Lepidium spp.
    Sinapis arvensis    Raphanus spp.
    etc.;
Geraniaceae, such as
    Erodium spp.    Geranium spp.
    etc.;
Portulaceceae, such as
    Portulaca spp.    etc.;
Primulaceae, such as
    Anagallis arvensis    Lysimachia spp.
    etc.
Rubiaceae, such as
    Richardia spp.    Diodia spp.
    Galium spp.    etc.;
Scrophulariaceae, such as
    Linaria spp.    Digitalis spp.
    Veronica spp.    etc.;
Solanaceae, such as
    Physalis spp.    Nicandra spp.
    Solanum spp.    Datura spp.
    etc.;
Urticaceae, such as
    Urtica spp.
Violaceae, such as
    Viola spp.    etc.;

Zygophyllaceae, such as
  Tribulus terrestris    etc.;
Euphorbiaceae, such as
  Mercurialis annua    Euhporbia spp.
Umbelliferae, such as
  Daucus carota    Ammi majus
  Aethusa cynapium    etc.;
Commelinaceae, such as
  Commelina spp.    etc.;
Labiatae, such as
  Lamium spp.    Galeopsis spp.
  etc.;
Leguminosae, such as
  Medicago spp.    Sesbania exaltata
  Trifolium spp.    Cassia spp.
  Vicia spp.    Lathyrus spp.
  etc.;
Plantaginaceae, such as
  Plantago spp.    etc.;
Polygonaceae, such as
  Polygonum spp.    Fagopyrum spp.
  Rumex spp.    etc.;
Alizoaceae, such as
  Mollugo verticillata    etc.;
Amaranthaceae, such as
  Amaranthus spp.    etc.;
Boraginaceae, such as
  Amsinckia spp.    Anchusa spp.
  Myostis spp.    Lithospermum spp.
  etc.;
Caryophyllaceae, such as
  Stellaria spp.    Silene spp.
  Spergula spp.    Cerastium spp.
  Saponaria spp.    Agrostemma githago
  Scleranthus annuus    etc.;
Chenopodiaceae, such as
  Chenopodium spp.    Atriples spp.
  Kochia spp.    Monolepsis nuttalliana
  Salsola Kali    etc.;
Lythraceae, such as
  Cuphea spp.    etc.;
Oxalidaceae, such as
  Oxalis spp.
Ranunculaceae, such as
  Ranunculus spp.    Adonis spp.
  Delphinium spp.    etc.;
Papaveraceae, such as
  Papaver spp.    Fumaris officinalis
  etc.;
Onagraceae, such as
  Jussiaea spp.    etc.;
Rosaceae, such as
  Alchemillia spp.    Potentilla spp.
  etc.;
Potamogetonaceae, such as
  Potamogeton spp.    etc.;
Najadaceae, such as
  Najas spp.    etc.;
Equisetaceae
  Equisetum spp.    etc.;
Marsileaceae, such as
  Marsilea quadrifolia    etc.;
Polypodiaceae
  Pteridium quilinum
Alismataceae, such as
  Alisma spp.    Sagittaria sagittifolia
  etc.

The agents according to the invention may be used in cereal crops such as

Avena spp.    Sorghum
Triticum spp.    Zea mays
Hordeum spp.    Panicum miliaceum
Secale spp.    Oryza spp.
Saccharum officinarum
and in dicotyledonous crops such as Cruciferae, e.g.
  Brassica spp.    Raphanus spp.
  Sinapis spp.    Lepidium spp
Compositae, e.g.
  Lactuca spp.    Carthamus spp.
  Helianthus spp.    Scorzonera spp.
Malvaceae, e.g.
  Gossypium hirsutum
Leguminosae, e.g.
  Medicago spp.    Phaseolus spp.
  Trifolium spp.    Arachis spp.
  Pisum spp.    Glycine max.
Chenopodiaceae, e.g.
  Beta vulgaris
  Spinacia spp.
Solanaceae, e.g.
  Solanum spp.    Capsicum annuum
  Nicotiania spp.
Linaceae, e.g.
  Linum spp.
Umbelliferae, e.g.
  Petroselinum spp.    Apium graveolens
  Daucus carota
Rosaceae, e.g.    Fragaria
Cucurbitaceae, e.g.
  Cucumis spp.    Cucurbita spp.
Liliaceae, e.g.
  Allium spp.
Vitaceae, e.g.
  Vitis vinifera
Bromeliaceae, e.g.
  Ananas sativus

EXAMPLE 4

In the greenhouse, the plants rice (*Oryza sativa*), soybeans (*Glycine max.*), Indian corn (*Zea mays*), wheat (*Triticum spp.*), yellow nutsedge (*Cyperus esculentus*), purple nutsedge (*Cyperus rotundus*), barnyardgrass (*Echinochloa crusgalli*), wild mustard (*Sinapis arvensis*), wild radish (*Raphainus raphanistrum*), chamomile (*Matricaria chamomilla*) and common lambsquarters (*Chenopodium album*) were treated at a growth height of from 2 to 17 cm with 1.5 kg per hectare of each of the following active ingredients, each being dispersed or emulsified in 500 liters of water per hectare:

I. 1-(α-ethoxy)-ethyl-3-isopropyl-2,1,3-benzothiadiazin-(4)-one-2,2-dioxide

II. 1-(α-methoxy)-ethyl-3-isopropyl-2,1,3-benzothiadiazin-(4)-one-2,2-dioxide

III. 1-(α-methoxy)-isobutyl-3-isopropyl-2,1,3-benzothiadiazin-(4)-one-2,2-dioxide IV. 1-(α-isobutyloxy)-ethyl-3-isopropyl-2,1,3-benzothiadiazin-(4)-one-2,2-dioxide V. 1-(α-octadecyloxy)-ethyl-3-isopropyl-2,1,3-benzothiadiazin-(4)-one-2,2-dioxide and, for comparison, VI. 3-methyl-2,1,3-benzothiadiazin-(4)-one-2,2-dioxide VII. 3-isopropyl-2,1,3-benzothiadiazin-(4)-one-2,2-dioxide.

After 3 to 4 weeks it was ascertained that compounds I to V had a better herbicidal action than VI, combined with the same crop plant compatibility.

The results are given below:

| Active ingredient kg/ha | I 1.5 | II 1.5 | III 1.5 | IV 1.5 | V 1.5 | VI 1.5 | VII 1.5 |
|---|---|---|---|---|---|---|---|
| Crop plants: | | | | | | | |
| Oryza sativa | 0 | 0 | 0 | 0 | 0 | 0 | 0 |
| Glycine max | 0 | 0 | 0 | 0 | 0 | 0 | 5 |
| Zea mays | 0 | 0 | 0 | 0 | 0 | 0 | 0 |
| Tricticum spp. | 0 | 0 | 0 | 0 | 0 | 0 | 0 |
| Unwanted plants: | | | | | | | |
| Cyperus esculentus | 80 | 50 | 30 | 30 | 30 | 0 | 80 |

| Active ingredient kg/ha | I 1.5 | II 1.5 | III 1.5 | IV 1.5 | V 1.5 | VI 1.5 | VII 1.5 |
|---|---|---|---|---|---|---|---|
| Cyperus rotundus | 80 | 50 | 30 | 30 | 30 | 0 | 80 |
| Echinochloa crus-galli | 50 | 30 | 30 | 30 | 30 | 0 | 10 |
| Sinapis arvensis | 100 | 100 | 100 | 100 | 100 | 80 | 95 |
| Raphanus raphanistrum | 100 | 100 | 100 | 100 | 100 | 80 | 80 |
| Matricaria chamomilla | 100 | 100 | 90 | 90 | 90 | 85 | 85 |
| Chenopodium album | 100 | 100 | 95 | 90 | 90 | 85 | 85 |

0 = no damage
100 = complete destruction

EXAMPLE 5

In the greenhouse the plants cotton (Gossypium hirsutum) and wild mustard (Sinapis arvensis) were treated at a growth height of from 2 to 10 cm with 1 kg per hectare of each of the following active ingredients, each being emulsified or dispersed in 500 liters of water per hectare:

I. 1-(2'-methyltetrahydrofuranyl-5')-3-isopropyl-2,1,3-benzothiadiazin-(4)-one-2,2-dioxide II. 1-(4'-methyltetrahydropyranyl-6')-3-isopropyl-2,1,3-benzothiadiazin-(4)-one-2,2-dioxide III. 1-(2,2'-dimethyltetrahydrofuranyl-5')-3-isopropyl-2,1,3-benzothiadiazin-(4)-one-2,2-dioxide and, for comparison, IV. 3-isopropyl-2,1,3-benzothiadiazin-(4)-one-2,2-dioxide.

After 2 to 3 weeks it was ascertained that compounds I to III had better crop plant compatibility than IV, combined with the same herbicidal action.

The results are given below:

| Active ingredient kg/ha | I 1 | II 1 | III 1 | IV 1 |
|---|---|---|---|---|
| Crop plant: Gossypium hirsutum | 0 | 10 | 0 | 30 |
| Unwanted plant: Sinapis arvensis | 100 | 100 | 100 | 100 |

0 = no damage
100 = complete destruction

EXAMPLE 6

In the greenhouse, the plants rice (Oryza sativa), Indian corn (Zea mays) soybeans (Glycine max.), wheat (Triticum aestivum), barley (Hordeum vulgare), rye (Secale cereale), wild mustard (Sinapis arvensis) and yellow nutsedge (Cyperus esculentus) were treated at a growth height of from 3 to 23 cm with 4 kg per hectare of each of compounds I to III (designations as in Example 5), each being dispersed or emulsified in 500 liters of water per hectare.

After 2 to 3 weeks it was ascertained that active ingredients I to II had excellent crop plant compatibility and a good herbicidal action.

The results are given below:

| Active ingredient kg/ha | I 4 | II 4 | III 4 |
|---|---|---|---|
| Crop plants: | | | |
| Oryza sativa | 0 | 0 | 0 |
| Zea mays | 0 | 0 | 0 |
| Glycine max. | 0 | 0 | 0 |
| Triticum aestivum | 0 | 0 | 0 |
| Hordeum cereale | 0 | 0 | 0 |
| Unwanted plants: | | | |
| Sinapis arvensis | 100 | 100 | 100 |
| Cyperus esculentus | 80 | 100 | 100 |

0 = no damage
100 = complete destruction

We claim:

1. A substituted 2,1,3-benzothiadiazin-(4)-one-2,2-dioxide of the formula

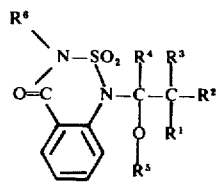

where $R^1$, $R^2$, $R^3$ and $R^4$ are hydrogen or lower alkyl, $R^5$ is an alkyl radical of 1 to 20 carbon atoms, $R^1$ and $R^5$ may also be combined to form a chain containing 2 or 3 methylene radicals, and $R^6$ is an alkyl radical of 1 to 10 carbon atoms or a lower alkyl substituted by fluoro, chloro or cyclohexyl.

2. 1-(α-ethoxy)-ethyl-3-isopropyl-2,1,3-benzothiadiazin-(4)-one-2,2-dioxide.

3. 1-(α-methoxy)-ethyl-3-isopropyl-2,1,3-benzothiadiazin-(4)-one-2,2-dioxide.

4. 1-(α-methoxy)-isobutyl-3-isopropyl-2,1,3-benzothiadiazin-(4)-one-2,2-dioxide.

5. 1-(α-isobutyloxy)-ethyl-3-isopropyl-2,1,3-benzothiadiazin-(4)-one-2,2-dioxide.

6. 1-(α-octadecyloxy)-ethyl-3-isopropyl-2,1,3-benzothiadiazin-(4)-one-2,2-dioxide.

7. 1-(2'-methyltetrahydrofuranyl-5')-3-isopropyl-2,1,3-benzothiadiazin-(4)-one-2,2-dioxide.

8. 1-(4'-methyltetrahydropyranyl-6')-3-isopropyl-2,1,3-benzothiadiazin-(4)-one-2,2-dioxide.

9. 1-(2',2'-dimethyltetrahydrofuranyl-5')-3-isopropyl-2,1,3-benzothiadiazin-(4)-one-2,2-dioxide.

* * * * *

UNITED STATES PATENT AND TRADEMARK OFFICE
CERTIFICATE OF CORRECTION

PATENT NO. : 3,935,200
DATED : January 27, 1976
INVENTOR(S) : Adolf Fischer et al It is certified that error appears in the above-identified patent and that said Letters Patent are hereby corrected as shown below:

In Column 1, formula II lines 45-50, delete " $-\underset{\underset{NH}{\backslash}}{SO}$ " and substitute -- $-\underset{\underset{NH}{\backslash}}{SO_2}$ --

In Column 3, Line 47, delete " methyl-(propen-(1)-ether " and substitute -- methyl-(propen-(1)-yl)-ether --

In Column 4, first line of Example 2, after "At 20°C" insert -- to 25°C --

Signed and Sealed this

Twenty-eighth Day of September 1976

[SEAL]

Attest:

RUTH C. MASON
*Attesting Officer*

C. MARSHALL DANN
*Commissioner of Patents and Trademarks*